United States Patent
Khanna

(10) Patent No.: US 11,534,336 B2
(45) Date of Patent: Dec. 27, 2022

(54) SELECTIVE CENTRAL NERVOUS SYSTEM TREATMENT CATHETER AND A METHOD OF USING THE SAME

(71) Applicant: Rohit Khanna, Daytona Beach, FL (US)

(72) Inventor: Rohit Khanna, Daytona Beach, FL (US)

( * ) Notice: Subject to any disclaimer, the term of this patent is extended or adjusted under 35 U.S.C. 154(b) by 863 days.

(21) Appl. No.: 16/131,394

(22) Filed: Sep. 14, 2018

(65) Prior Publication Data

US 2019/0083303 A1   Mar. 21, 2019

Related U.S. Application Data

(60) Provisional application No. 62/559,168, filed on Sep. 15, 2017.

(51) Int. Cl.

| A61F 7/00 | (2006.01) |
|---|---|
| A61F 7/12 | (2006.01) |
| A61M 25/00 | (2006.01) |
| A61M 19/00 | (2006.01) |
| A61M 1/00 | (2006.01) |
| A61M 27/00 | (2006.01) |
| A61M 3/02 | (2006.01) |

(52) U.S. Cl.
CPC ........... *A61F 7/12* (2013.01); *A61F 7/123* (2013.01); *A61M 1/85* (2021.05); *A61M 19/00* (2013.01); *A61M 25/003* (2013.01); *A61M 25/0026* (2013.01); *A61F 7/0085* (2013.01); *A61F 2007/0056* (2013.01); *A61F 2007/0096* (2013.01); *A61F 2007/126* (2013.01); *A61M 3/0229* (2013.01); *A61M 27/006* (2013.01); *A61M 2025/0024* (2013.01); *A61M 2025/0031* (2013.01); *A61M 2027/004* (2013.01); *A61M 2202/0464* (2013.01); *A61M 2205/3303* (2013.01); *A61M 2205/3344* (2013.01); *A61M 2205/366* (2013.01); *A61M 2205/3606* (2013.01); *A61M 2210/0693* (2013.01); *A61M 2210/1003* (2013.01); *A61M 2230/08* (2013.01); *A61M 2230/10* (2013.01); *A61M 2230/30* (2013.01); *A61M 2230/50* (2013.01)

(58) Field of Classification Search
CPC ............. A61F 7/123; A61F 7/0085; A61F 2007/0056; A61F 2007/126; A61M 2205/3606; A61M 27/006; A61M 2202/0464; A61M 2210/0693; A61M 2025/0037; A61M 25/007; A61M 25/0026
See application file for complete search history.

(56) References Cited

U.S. PATENT DOCUMENTS

| 4,904,237 A | 2/1990 | Janese |
| 5,395,316 A * | 3/1995 | Martin ............. A61M 25/0028 604/284 |
| 6,217,552 B1 | 4/2001 | Barbut et al. |
| 6,379,331 B2 | 4/2002 | Barbut et al. |

(Continued)

*Primary Examiner* — Ariana Zimbouski
(74) *Attorney, Agent, or Firm* — Wenderoth, Lind & Ponack, L.L.P.

(57) ABSTRACT

An apparatus and method use a catheter for specific and discriminate treatment of central nervous system disease. With the catheter, selective hypothermia to the brain and/or the spinal cord for injury protection can be achieved without the need for systemic cooling. The catheter is also capable of draining excess cerebrospinal fluid.

34 Claims, 10 Drawing Sheets

(56) References Cited

U.S. PATENT DOCUMENTS

| | | | |
|---|---|---|---|
| 6,527,798 B2 | 3/2003 | Ginsburg et al. | |
| 6,572,638 B1 * | 6/2003 | Dae | A61F 7/123 |
| | | | 607/96 |
| 6,682,503 B1 * | 1/2004 | Fariss | A61F 5/4405 |
| | | | 137/843 |
| 6,699,269 B2 | 3/2004 | Khanna | |
| 6,758,832 B2 | 7/2004 | Barbut et al. | |
| 6,929,656 B1 | 8/2005 | Lennox | |
| 7,004,961 B2 | 2/2006 | Wong et al. | |
| 7,144,418 B1 | 12/2006 | Lennox | |
| 8,123,789 B2 | 2/2012 | Khanna | |
| 2002/0082556 A1 * | 6/2002 | Cioanta | A61B 18/04 |
| | | | 604/113 |
| 2009/0247868 A1 * | 10/2009 | Chesnin | A61M 25/0032 |
| | | | 600/435 |
| 2012/0095536 A1 * | 4/2012 | Machold | A61F 7/123 |
| | | | 607/105 |
| 2012/0221082 A1 * | 8/2012 | Khanna | A61F 7/12 |
| | | | 607/105 |
| 2017/0095649 A1 * | 4/2017 | Vase | A61F 7/123 |

\* cited by examiner

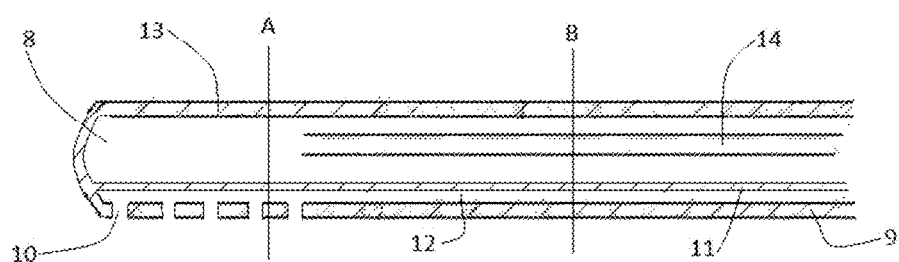
Fig. 2
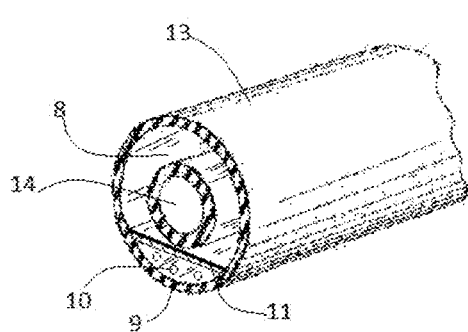 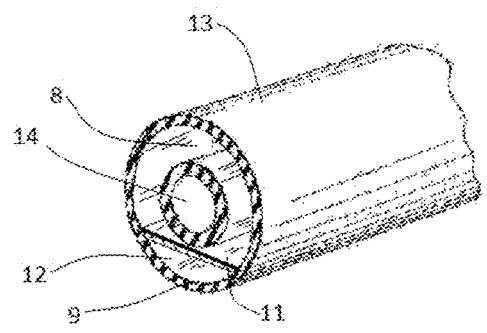
Fig. 3                    Fig. 4

SELECTIVE CENTRAL NERVOUS SYSTEM TREATMENT CATHETER AND A METHOD OF USING THE SAME

BACKGROUND

The present disclosure relates to a catheter for brain and spinal cord disease treatment. The disclosure more specifically relates to a catheter and a method for using the catheter to protect the brain and spinal cord by selectively altering the temperature of the central nervous system and draining cerebrospinal fluid (CSF).

Hypothermia has been shown to provide cerebral and spinal cord injury protection from trauma, ischemia, or hypoxia. Ischemia may occur from cardiac arrest, cardiac failure, stroke, head or spinal cord injury, aneurysm surgery, cardiac surgery, aortic dissection or aneurysm treatment or carotid surgery. Hypothermia is also effective in reducing increased intracranial pressure from cerebral swelling. The mechanisms involved in hypothermic cerebral protection are several-fold and include 1) reducing cerebral glucose and oxygen metabolism and decreasing lactate content following injury, 2) preventing disruption of the blood brain barrier and consequently reducing cerebral edema, 3) reducing endogenously toxic neurotransmitters like glutamate, glycine, aspartate, acetylcholine, and norepinephrine into the brain after injury, 4) inhibiting excessive calcium entry and intracellular calcium overload into neurons, 5) protecting membrane structural proteins like microtubule-associated protein-2, and 6) preventing diffuse axonal injury following brain trauma.

In general, the human brain and spinal cord are maintained at a constant temperature of approximately 37 to 38 degrees Celsius. Hypothermia is considered mild when the body temperature is 33 to 35 degrees Celsius, moderate between the temperatures of 28 to 32 degrees Celsius, and severe in the temperature range of 24 to 28 degrees Celsius. Most studies in humans have involved mild to moderate systemic hypothermia mainly because of the significant side effects that occur from induced systemic hypothermia. These include infection, cardiac arrhythmias, coagulopathy, renal failure, pneumonia, excessive shivering, as well as rewarming shock. In order to avoid these complications, the degree and duration of hypothermia have been mild and short, respectively, thereby limiting its effectiveness.

Generally, cooling of the brain has been accomplished through whole body cooling by using a cooling blanket, immersing the patient in ice, or cooling the blood through a cardiopulmonary bypass machine. A few methods have been described regarding selective brain and spinal cord hypothermia. These involve cooling the arterial vessel or blood supply to the brain or external cooling helmets, each with its own significant limitations.

Several catheters have been developed to induce systemic hypothermia by inserting them into the bloodstream. More recently catheters have been developed that can be inserted into the arterial vessels to the brain to induce selective brain hypothermia. These catheters are limited in their size and functionality by the small vessel lumen, as well as the inability to cool all the four major arterial vessels supplying blood to the brain, and are unable to cool the spinal cord. They also carry the risk of ischemic and thromboembolic stroke by either impairing the blood flow to the brain or dislodging clots that can develop in intra-arterial catheters.

External cooling helmets have limited effectiveness since the blood to the cooled scalp does not circulate into the brain and returns systemically which, along with the thickness of the skull, dilutes the hypothermic effect to the brain.

The prior art lacks specificity in the operational mechanism for the treatment of central nervous system disease. The prior art relates to cooling the whole body with external pads, intravascular cooling or a helmet. These systemic cooling approaches are countered by the body's own mechanisms of thermoregulation and, therefore, are rendered ineffective or achieve very minimal effects. In order to counteract the systemic cooling effect, selective central nervous system hypothermia by circulating a coolant in the cerebrospinal fluid space or directly cooling the central nervous system with a closed loop catheter has been utilized.

Selective brain and spinal cord cooling with the insertion of closed loop system catheters into the ventricular, subdural or epidural space was first described in U.S. Pat. No. 6,699,269 to Khanna. It also describes a catheter that expands with the circulation of a coolant in a closed loop system within the central nervous system. This avoids the side effects and complications seen from other methods of cooling. It also circumvents infection and fluid overload with exacerbation of brain swelling that can be potentially encountered with cooling systems involving direct circulation of a coolant into the cerebrospinal fluid space inside the skull or spinal canal. The Khanna U.S. Pat. No. 6,699,269 patent also describes cerebrospinal fluid drainage to relieve an increase in intracranial pressure (ICP). U.S. Pat. No. 8,123,789 and U.S. application Ser. No. 13/107,916 to Khanna also relate to a method and apparatus for selective central nervous system cooling with a catheter. Central nervous system diseases like trauma, stroke, hemorrhage, tumors, infection, surgery, etc. frequently lead to brain and/or spinal cord swelling and an increase in the central nervous system pressure. An increased central nervous system pressure, in turn, decreases the cerebral perfusion pressure and consequently the blood flow which further exacerbates the neurologic condition.

Aortic operations of the thoracic and abdominal aorta are not infrequently complicated by paraplegia. Paraplegia after a thoracic aortic aneurysm surgery is a devastating condition with high morbidity and poor quality of life, as well as mortality. Spinal ischemia following aortic surgery is a well-known complication. During thoracic or abdominal aortic aneurysm/dissection repair the intercostal/radicular arteries supplying blood to the spinal cord from the aorta, especially the Artery of Adamkiewicz, can be disrupted or occluded, impairing the blood flow to the spinal cord. Aortic clamping to facilitate aneurysm repair can also result in a reduction of spinal cord perfusion, especially if the clamp time is longer than 45 minutes, often resulting in paralysis. Spinal cord hypothermia and CSF drainage can reduce risk of paraplegia in these patients.

The prior art lacks any specificity in achieving the optimal neurologic outcome.

What is desired, therefore, is a method and apparatus with high specificity for thermoregulation, selective central nervous system cooling and cerebrospinal fluid drainage for the treatment of central nervous system disease.

SUMMARY

The present disclosure relates to an apparatus and methodology for specific and discriminate treatment of central nervous system disease achieved by performing selective hypothermia to the brain and/or the spinal cord for injury protection without the need for systemic cooling, as well as providing drainage of any excess cerebrospinal fluid through the apparatus.

Prior art based on indiscriminate and non-specific treatment fails to achieve the full extent of central nervous system disease treatment. For instance, the degree of hypothermia is associated with the extent of neurologic deficit prevention. Hypothermia induction with a temperature between 24-28 degrees Celsius provides better neurologic protection compared to temperatures between 33-35 degrees Celsius.

The extent of central nervous system or intracranial pressure decrease is associated with decreased neurologic deficits and it is desirable to keep the ICP, for example, less than 20 mmHg or, for example, less than 10 mmHg. ICP decreasing measures include the extent of CSF drainage, degree of hypothermia, decreasing cerebral/spinal cord edema, decreasing central nervous system blood volume, reducing neuronal metabolism, and improving central nervous system blood flow. ICP reduction can be accomplished by adjusting the amount of cerebrospinal fluid drainage, as well the temperature of the central nervous system. Medications like mannitol, hyperosmolar therapy, and hypertonic saline also decrease brain or spinal cord edema by removing excess fluid through an osmotic effect and reduce elevated ICP. ICP reduction by reducing the brain/spinal cord metabolism can also be accomplished with medications like barbiturates, propofol, and pentobarbitol. The ICP can either be monitored through sensors in the catheter, an external pressure transducer connected to the catheter drainage lumen, or alternatively by free drainage maintaining the external CSF drain reservoir/bag at a 10 mmHg level or any other desired level. Maintaining the drainage reservoir at 13 cm above the external auditory meatus equates to 10 mm Hg pressure and an ICP above this limit will be treated by free flowing CSF drainage until this pressure is achieved. In order to avoid spinal cord ischemia in patients undergoing either surgical or endovascular treatment of aortic disease, several strategies are proposed to avoid this complication. These include the drainage of cerebrospinal fluid, raising the systemic blood pressure with inotropic medications and intravascular volume, induction of selective central nervous system hypothermia, and re-anastomosis of the disrupted radicular blood vessels supplying blood from the spinal cord to the aorta.

Prior use of hypothermia to prevent spinal cord injury has demonstrated clear benefits, but there are methodological drawbacks limiting application of this approach in patients. In the spinal cord, regional spinal cord hypothermia increases spinal cord ischemia tolerance. Hypothermia decreases the extent of CSF glutamate, neurotoxins, and metabolite release and corresponding development of neuronal damage after spinal cord injury. A benefit in patients after selective spinal hypothermia to prevent spinal cord ischemia has also been demonstrated. CSF drainage and avoidance of hypotension is utilized to minimize spinal cord ischemia. It has been shown that subdural and epidural infusion cooling produces localized spinal cord hypothermia concurrently with uniformly distributed pressure increases and can result in spinal cord ischemia. Infusion of a coolant into the subdural, epidural or cerebrospinal fluid space increases the spinal fluid volume thereby concurrently increasing the pressure. What is therefore desired is a method that combines selective hypothermia with a closed loop catheter without the infusion of coolant into the cerebrospinal fluid or epidural space along with the capability of CSF drainage.

Hypothermia can also alter cerebral vasoreactivity, and may enhance volatile anesthetic-induced vasodilatation of cerebral vessels which can lead to decreased cerebral blood flow and an increase in ICP. What is desired is a device and methodology that can mitigate this risk and preserve neurologic function in patients requiring anesthesia.

For selective brain and/or spinal cord cooling, in an embodiment of the present disclosure, a flexible heat exchange catheter is inserted into the cerebrospinal fluid space. The catheter has an inflow and outflow lumen for circulation of a coolant in a closed loop system by an external regulator and a drainage lumen. The drainage lumen has holes at the distal end that allow for drainage of cerebrospinal fluid, as well as intracranial pressure monitoring similar to a ventriculostomy or spinal intrathecal drain. An external regulator controls the coolant temperature and circulation rate and maintains the central nervous system pressure within a desirable range. An external CSF collection chamber also regulates the amount of CSF drainage and maintains a desired central nervous system pressure.

Cerebrospinal fluid is produced by the choroid plexus inside the brain lateral ventricles. The two lateral ventricles communicate with each other through the third ventricle which also opens into the fourth ventricle. The lateral ventricles also communicate with the cerebrospinal fluid in the basal cisterns surrounding the brain stem through the choroidal fissure. The fourth ventricle communicates with the subarachnoid space through the foramen of Magendie and Luschka. The subarachnoid space extends from around the brain, brainstem, and spinal cord. Essentially, all of the central nervous system structures and, in particular, the brain and spinal cord either are surrounded by or contain cerebrospinal fluid. A methodology that cools the cerebrospinal fluid allows for a faster and more uniform selective central nervous system hypothermia induction and also avoids the systemic toxic side effects of generalized body or blood vessel cooling. The present disclosure also relates induction of selective central nervous system hypothermia by dilating a balloon in the distal portion of the device in a pulsating and/or peristaltic manner. Pulsating or peristaltic balloon dilation not only increases the surface area for heat exchange, but also facilitates movement of the cooled cerebrospinal fluid to enable a faster and more uniform cooling of the brain and/or spinal cord.

The device involves circulating a coolant by means of a pump at a controlled temperature flow rate through the closed loop catheter and monitoring the temperature of the central nervous system. To achieve a preprogrammed temperature over a period of time, feedback adjustment of the coolant temperature and flow rate to the measured cerebrospinal fluid temperature with a computer automated control system can also be undertaken. Feedback adjustment of the cerebrospinal fluid drainage to the measured intrathecal pressure to achieve preprogrammed pressure targets over a period of time with an automated system can also be undertaken.

BRIEF DESCRIPTION OF THE DRAWINGS

FIG. 2 is a longitudinal cross-sectional view of a first embodiment of the catheter.

FIG. 3 is a partial sectional view of the first embodiment of the catheter along line A in FIG. 2.

FIG. 4 is a partial sectional view of the first embodiment of the catheter along line B in FIG. 2.

DETAILED DESCRIPTION

Figure 1:
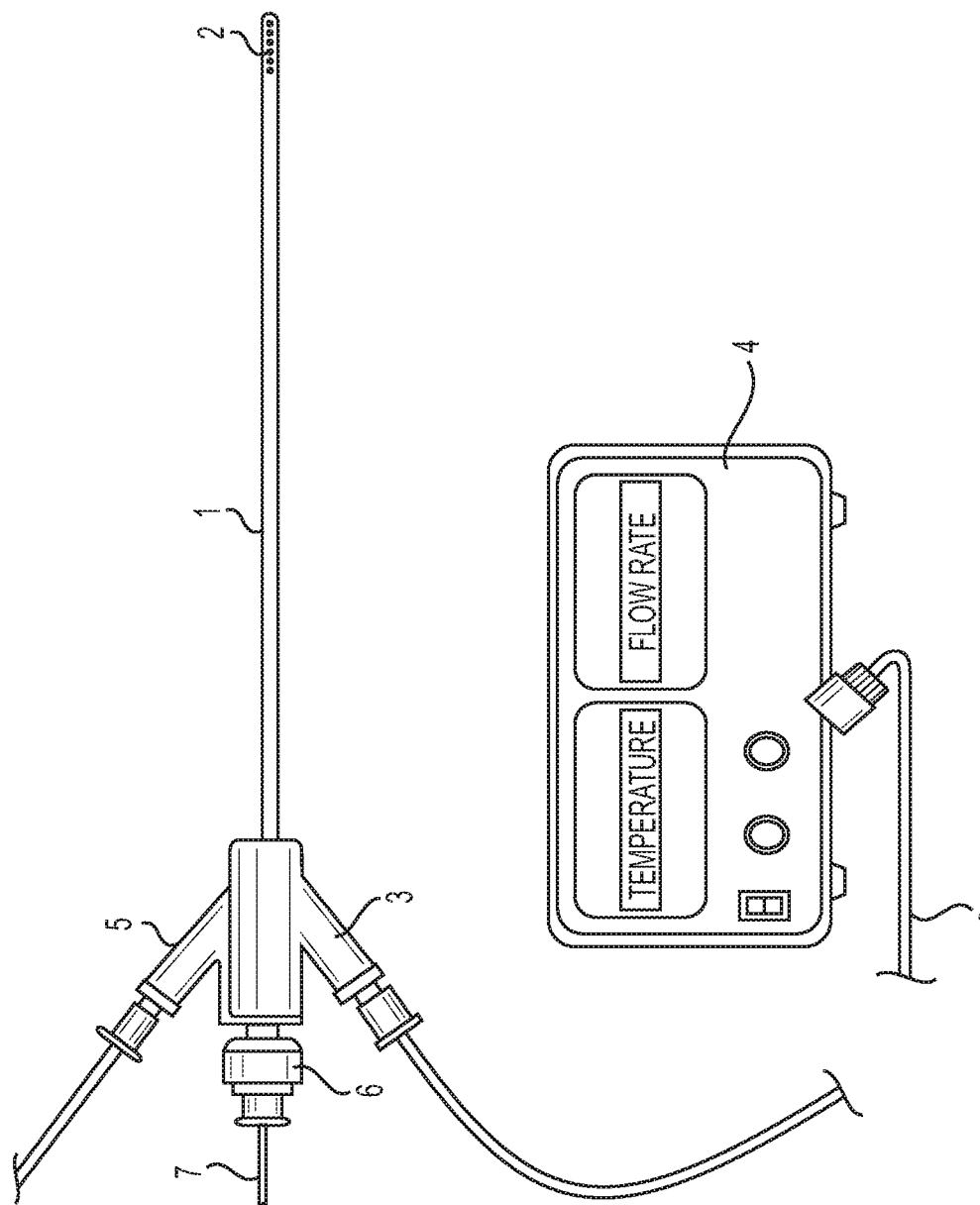
FIG. 1 is a schematic view of an embodiment of a flexible catheter connected to an external flow regulator and cooler.

As shown in FIG. 1, a hypothermia catheter 1 has a distal component comprising drainage holes 2. Portions 3 and 5 connect the two closed loop catheter lumens of the catheter 1 to a flow regulator and cooler 4 for circulation of a coolant. The extent of the central hypothermia induction can be controlled by adjusting the coolant temperature and flow rate with the flow regulator and cooler 4. The catheter 1 also comprises a proximal portion 6 that connects the drain lumen to a drainage bag. The drainage proximal portion 6 can also be connected to a vacuum negative pressure device or bag to facilitate drainage. The extent of cerebrospinal fluid drainage can be controlled to achieve a desired central nervous system pressure. A stylet 7 can also be placed inside the drain lumen of the catheter 1 to assist in the placement of the flexible catheter 1 inside the head or spine. The stylet 7 provides for catheter stiffness to target the exact placement location. The stylet 7 or the catheter 1 can also be registered with markers for camera sensors for navigational purpose. This allows for stereotactic placement of the catheter with image guidance. Alternatively, the catheter 1 can also contain or be embedded with radio-opaque markers to visualize its location on x-rays or fluoroscopy.

The catheter 1 can be inserted in the lateral ventricle of the brain similar to a ventriculostomy drain via, for example, a twist drill hole in the skull, a burr hole or during a craniotomy procedure. The option of a distal balloon increases the surface area to allow faster and more efficient heat exchange and selective cooling by convection to the CSF space, as well as the possibility of direct contact with the ventricle wall lining. An effective spinal cerebrospinal fluid space location of the catheter 1 is in the lumbar location, but can also include the cervical or thoracic spine. Alternatively, the catheter 1 can be inserted through the lumbar spine with the distal tip positioned in the thoracic spine. The catheter 1 cools the spinal cord by cooling the CSF, as well as by direct spinal cord surface contact. The catheter 1 can, for example, be inserted post-operatively after a laminectomy, discectomy, or corpectomy. The catheter 1 can also be inserted through a percutaneous technique similar to placement of a spinal drain or lumbar puncture. X-ray or fluoroscopy can also be used to locate the correct spinal placement of the catheter 1.

As shown in FIGS. 2-4, a first embodiment of the catheter 1 comprises an outside wall including an outside coaxial wall superior portion 13 and an inferior wall portion 9, and a straight inside wall 11. The inside wall 11 divides the lumen of the catheter 1 into two parts 8 and 12 (i.e., two lumens) which do not communicate. The lumen 8 comprises another lumen 14 defined by another inside wall that communicates with the lumen 8 at the distal portion of the catheter 1 and circulates a coolant in a closed format through, for example, the flow regulator and cooler 4 placed external to the body. The other inside wall defining the lumen 14 is coaxial with the outside wall.

The catheter distal end is placed inside the desired central nervous system location. The distal portion can also have one or more sensors (pressure, temperature, etc.). The distal portion of the inferior wall portion 9 can have one or more holes 10 that allow the lumen 12 to communicate with the outside environment, and allow for the drainage of cerebrospinal fluid, as well as the monitoring of the central nervous system (e.g., the intracranial pressure).

Figure 5:
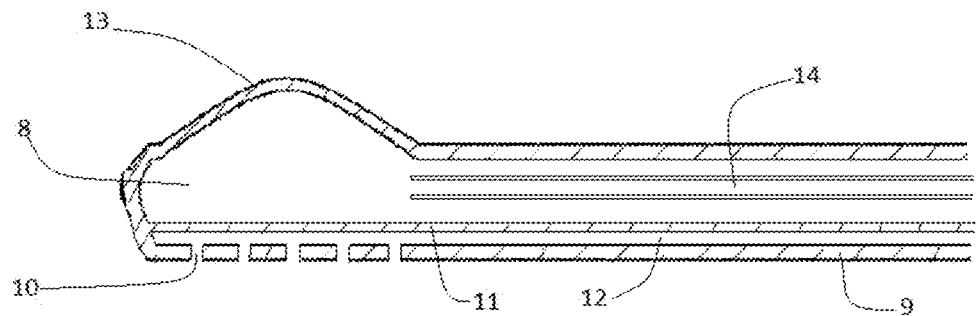
FIG. 5 is a longitudinal cross-sectional view of a modified first embodiment of the catheter with a dilated distal portion.

FIG. 5 shows a modified first embodiment of the catheter 1 with the distal portion of the outside coaxial wall superior portion 13 and the lumen 8 capable of expanding to increase the surface area for heat exchange. The expanding can occur in a peristaltic and/or pulsating manner. To achieve this expansion, the distal portion of the outside coaxial wall superior portion 13 can include at least one balloon that is expandable. The inferior wall portion 9 and the lumen 12 do not expand.

The distal portion of the outside coaxial wall superior portion 13 is capable of expanding into one or more of the following: an oval shape, a round shape, a cylindrical shape, a triangular shape, a double balloon shape, a helical shape, at an angle to the catheter, a shape of a portion of or an entire lateral ventricle, a shape of a frontal horn of a lateral ventricle, a shape of body of a lateral ventricle, a shape of an occipital horn of a lateral ventricle, a shape of a third ventricle, a shape of an operative area in a brain or spine, a shape of a cisterna magna, and a shape of a spinal canal.

Figure 6:
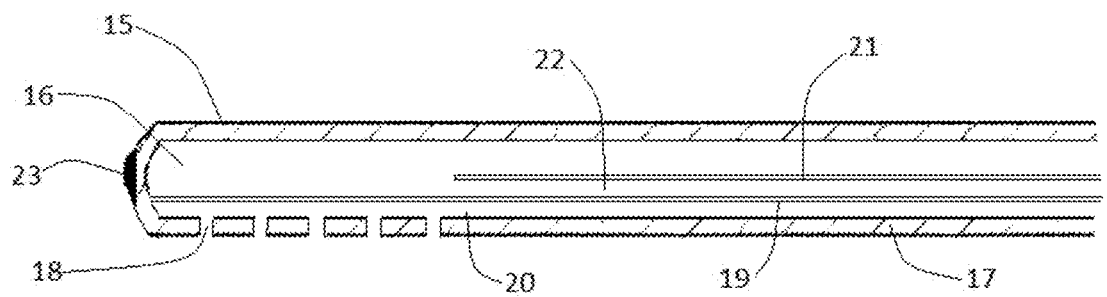
FIG. 6 is a longitudinal cross-sectional view of a second embodiment of the catheter.
Figure 7:
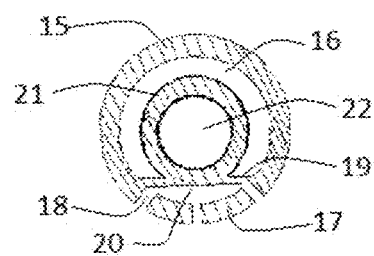
FIG. 7 is a cross-sectional view of the second embodiment of the catheter in FIG. 6.

In a second embodiment, as shown in FIGS. 6 and 7, the catheter 1 comprises an outside wall including an outside coaxial wall superior portion 15 and an inferior wall portion 17, and a straight inside wall 19. The inside wall 19 divides the lumen defined by the outside wall of the catheter 1 into two parts 16 and 20 (i.e., two lumens) which do not communicate. The lumen 16 comprises another coaxial lumen 22 that communicates with the lumen 16 at the distal portion of the catheter 1 and circulates a coolant in a closed format through, for example, the flow regulator and cooler 4 placed external to the body. The lumen 20 can be rectangular shaped. The lumen 22 is defined by a superior inside wall 21 and the inferior inside wall 19, which are connected. The superior inside wall 21 is coaxial with the outside wall.

The distal end of the catheter 1 is placed inside the desired central nervous system location. A distal portion 23 of the catheter 1 can also have one or more sensors (pressure, temperature, etc.). The distal portion of the inferior wall portion 17 can have one or more holes 18 that allow the lumen 20 to communicate with the outside environment, and allow for the drainage of cerebrospinal fluid, as well as the monitoring of the central nervous system (e.g., the intracranial pressure).

Figure 8:
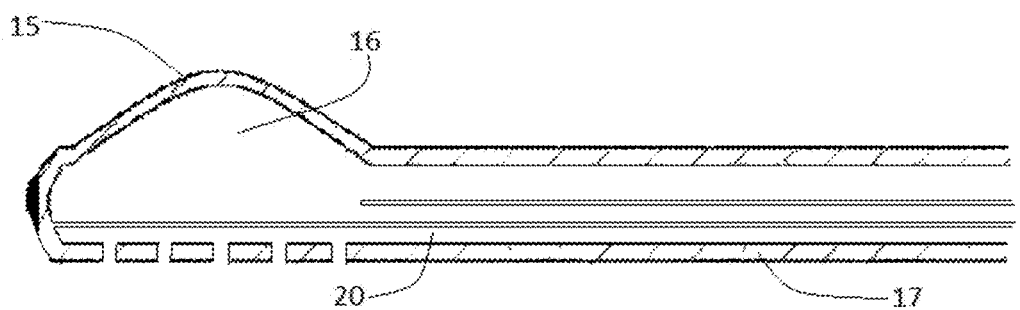
FIG. 8 is a cross-sectional longitudinal view of a modified second embodiment of the catheter.
Figure 9:
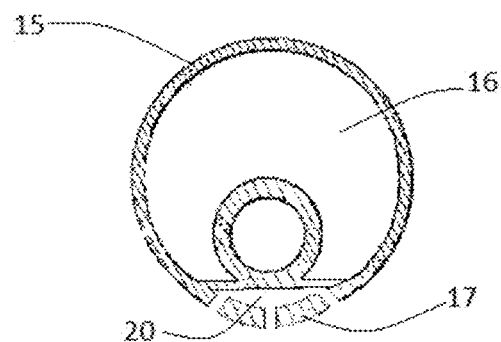
FIG. 9 is a cross-sectional view of the modified second embodiment of the catheter in FIG. 8.

FIGS. 8 and 9 show a modified second embodiment of the catheter 1 with the distal portion of the outside coaxial wall superior portion 15 and the lumen 16 capable of expanding to increase the surface area for heat exchange. The expanding can occur in a peristaltic and/or pulsating manner. To achieve the expansion, the distal portion of the outside coaxial wall superior portion 15 can include at least one balloon that is expandable. The inferior wall portion 17 and the lumen 20 do not expand.

The distal portion of the outside coaxial wall superior portion 15 is capable of expanding into one or more of the following: an oval shape, a round shape, a cylindrical shape, a triangular shape, a double balloon shape, a helical shape, at an angle to the catheter, a shape of a portion of or an entire lateral ventricle, a shape of a frontal horn of a lateral ventricle, a shape of body of a lateral ventricle, a shape of an occipital horn of a lateral ventricle, a shape of a third ventricle, a shape of an operative area in a brain or spine, a shape of a cisterna magna, and a shape of a spinal canal.

Figure 10:
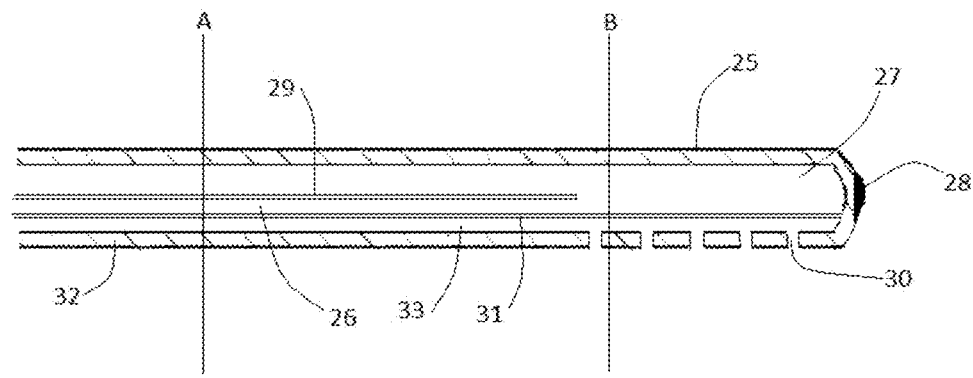
FIG. 10 is a longitudinal cross-sectional view of a third embodiment of the catheter.
Figure 11:
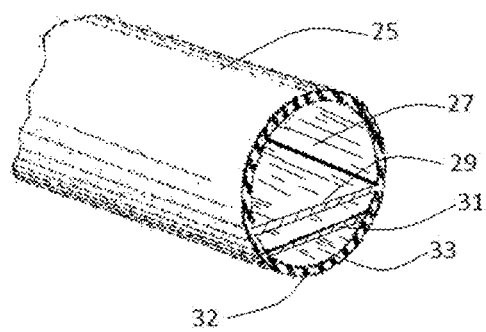
FIG. 11 is a partial sectional view of the third embodiment of the catheter along line A in FIG. 10.
Figure 12:
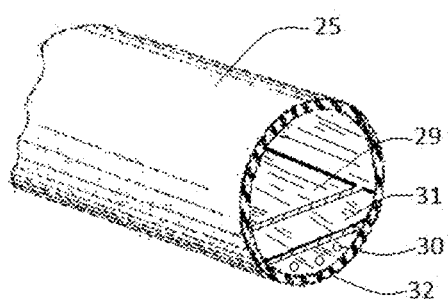
FIG. 12 is a partial sectional view of the third embodiment of the catheter along line B in FIG. 10.

In a third embodiment, as shown in FIGS. 10-12, the catheter 1 comprises an outside wall including an outside coaxial wall superior portion 25 and an inferior wall portion 32, and straight inside walls 29 and 31. The inside wall 29 divides the lumen defined by the outside wall of the catheter 1 into two parts 26 and 27 (i.e., two lumens) which communicate at the distal portion of the catheter 1 and circulate a coolant in a closed loop by way of, for example, the flow regulator and cooler 4 placed external to the body. The inside straight wall 31 and the inferior wall portion 32 define another lumen 33 which communicates with the outside environment through one or more holes 30 at the distal end of the inferior wall portion 32. The catheter distal end is placed inside the desired central nervous system location. A distal portion 28 of the catheter 1 can also comprise one or more sensors (pressure, temperature, etc.).

Figure 13:
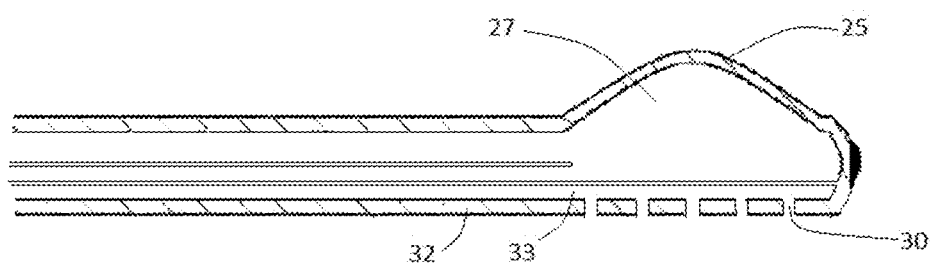
FIG. 13 is a longitudinal cross-sectional view of a modified third embodiment of the catheter with a dilated distal portion.

FIG. 13 shows a modified third embodiment of the catheter 1 with the distal portion of the outside coaxial wall superior portion 25 and the lumen 27 capable of expanding to increase the surface area for heat exchange. The expanding can occur in a peristaltic and/or pulsating manner. To achieve expansion, the distal portion of the outside coaxial wall superior portion 25 can include at least one balloon that is expandable. The inferior wall portion 32 and the lumen 33 do not expand.

The distal portion of the outside coaxial wall superior portion 25 is capable of expanding into one or more of the following: an oval shape, a round shape, a cylindrical shape, a triangular shape, a double balloon shape, a helical shape, at an angle to the catheter, a shape of a portion of or an entire lateral ventricle, a shape of a frontal horn of a lateral ventricle, a shape of body of a lateral ventricle, a shape of an occipital horn of a lateral ventricle, a shape of a third ventricle, a shape of an operative area in a brain or spine, a shape of a cisterna magna, and a shape of a spinal canal.

Figure 14:
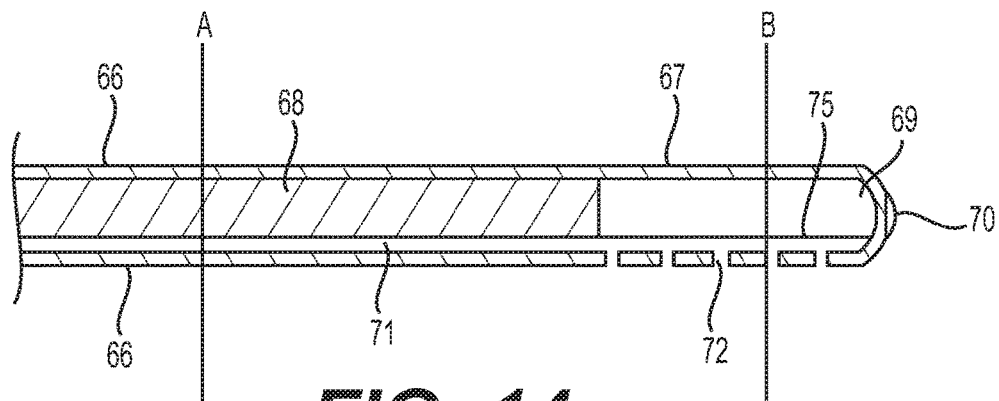
FIG. 14 is a longitudinal cross-sectional view of a fourth embodiment of the catheter.
Figure 15:
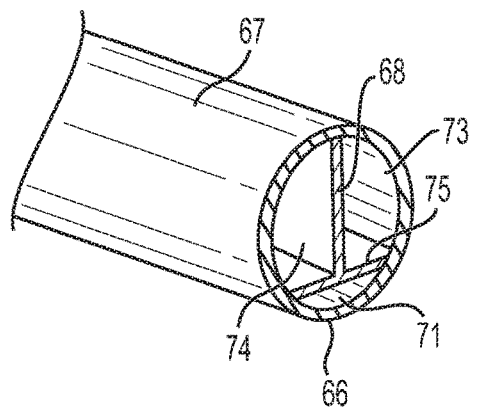
FIG. 15 is a partial sectional view of the fourth embodiment of the catheter along line A in FIG. 14.
Figure 16:
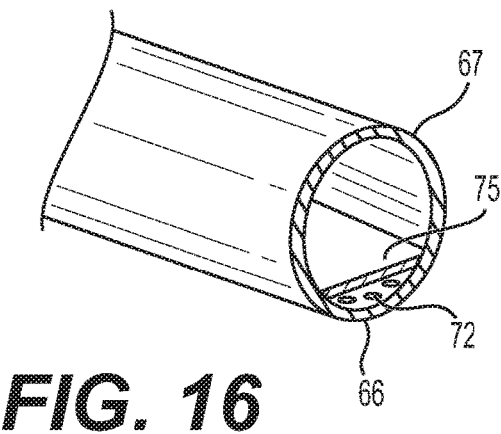
FIG. 16 is a partial sectional view of the fourth embodiment of the catheter along line B in FIG. 14.

In a fourth embodiment of the catheter 1, as shown in FIGS. 14-16, the catheter 1 comprises an outside wall including an outside coaxial wall superior portion 67 and an inferior wall portion 66, and two straight inside walls 68 and 75. The two straight inside walls 68 and 75 are orthogonal to each other. The inside wall 68 divides the lumen of the catheter 1 into two parts 73 and 74 (i.e., two lumens) which communicate at a distal portion 69 of the catheter 1 and circulate a coolant in a closed loop via, for example, the flow regulator and cooler 4.

The inside straight wall 75 and the inferior wall portion 66 define a lumen 71 which communicates with the outside environment through holes 72 at a distal end of the inferior wall portion 66. This allows for the drainage of cerebrospinal fluid, as well as the monitoring of the central nervous system (e.g., the intracranial pressure). The catheter distal end is placed inside the desired central nervous system location. The distal portion 70 can have one or more sensors (pressure, temperature, etc.).

Figure 17:
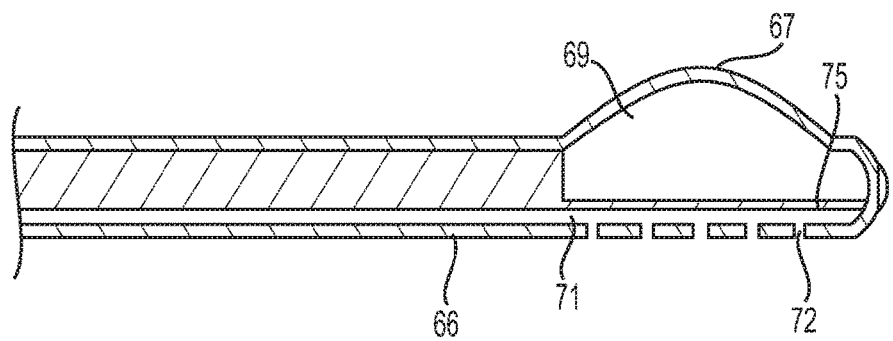
FIG. 17 is a longitudinal cross-sectional view of a modified fourth embodiment of the catheter with a dilated distal portion.

FIG. 17 shows a modified fourth embodiment of the catheter 1 with the distal portion of the outside coaxial wall superior portion 67 and the lumen 69 capable of expanding to increase the surface area for heat exchange with circulation of the coolant in the closed-loop. The expanding can occur in a peristaltic and/or pulsating manner. To achieve this expansion, the distal portion of the outside coaxial wall superior portion 67 can include at least one balloon that is expandable. The inferior wall portion 66 and the lumen 71 do not expand.

The distal portion of the outside coaxial wall superior portion 67 is capable of expanding into one or more of the following: an oval shape, a round shape, a cylindrical shape, a triangular shape, a double balloon shape, a helical shape, at an angle to the catheter, a shape of a portion of or an entire lateral ventricle, a shape of a frontal horn of a lateral ventricle, a shape of body of a lateral ventricle, a shape of an occipital horn of a lateral ventricle, a shape of a third ventricle, a shape of an operative area in a brain or spine, a shape of a cisterna magna, and a shape of a spinal canal.

Figure 18:
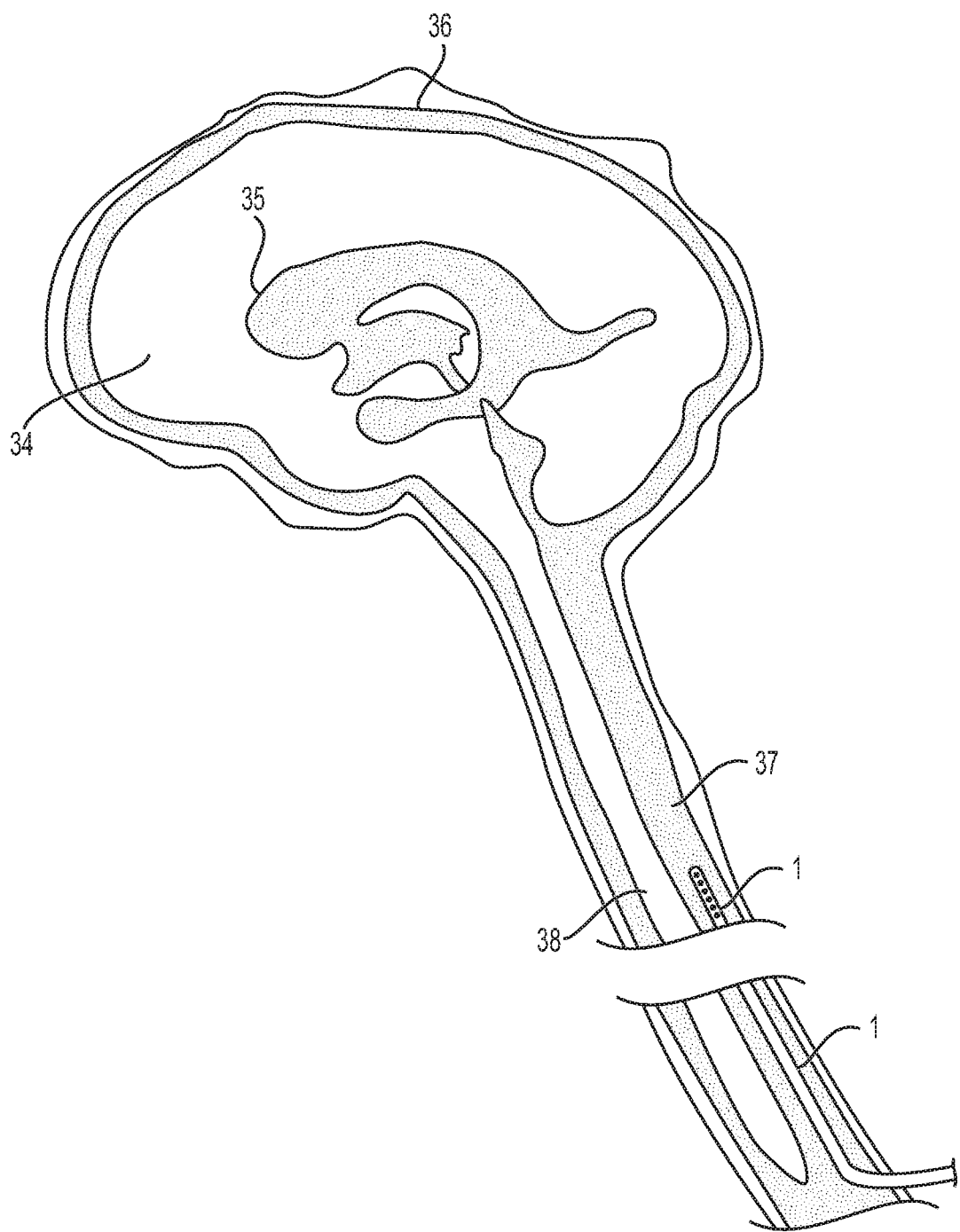
FIG. 18 is a schematic view of the central nervous system and cerebrospinal fluid space with the catheter in the spinal subdural/subarachnoid space.
Figure 19:
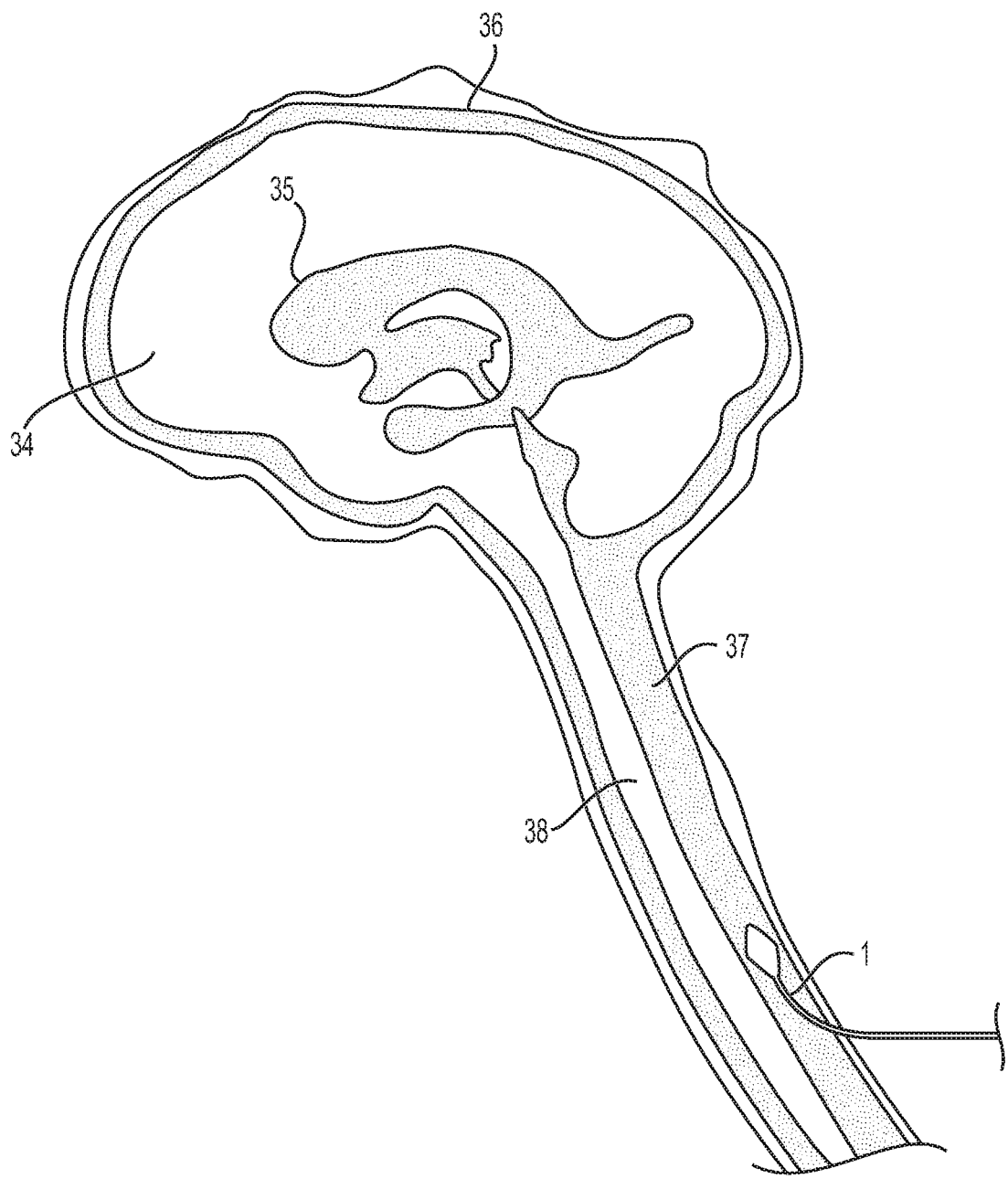
FIG. 19 is a schematic view of the catheter with the distal balloon dilation capability placed in the spinal subdural/subarachnoid space.

As shown in FIGS. 18 and 19, the brain 34 contains cerebrospinal fluid inside the ventricles 35 and is also surrounded by cerebrospinal fluid 36 which is in communication with cerebrospinal fluid 37 around the spinal cord 38. Cooling of the cerebrospinal fluid with the catheter 1 inserted in the spine intrathecal space 37 by circulating a coolant through the lumens of the catheter 1 designed to allow the coolant to circulate in a closed loop provides for selective hypothermia of the brain and spinal cord. The performing of the selective hypothermia can be accomplished by adjusting a temperature and/or the flow rate of the coolant circulating through the catheter 1 with, for example, the flow regulator and cooler 4.

The catheter 1 also provides for drainage of cerebrospinal fluid and lowering the intracranial and spinal pressures via the other lumen of the catheter 1 that communicates with the outside environment through one or more holes in the catheter 1. The draining of the cerebrospinal fluid can be regulated by one or more of: a valve that opens at a set pressure, an anti-reflux valve, an automated collection chamber that allows fluid drainage at a set pressure, a drainage bag that allows fluid drainage at a set pressure based on location of a bag relative to anatomical landmarks.

As shown in FIG. 19, facilitating circulation of the cooled cerebrospinal fluid provides for a faster brain and spinal cord cooling. The cerebrospinal fluid circulation can be facilitated by the catheter 1 with a distal balloon placed in the cerebrospinal fluid 37 that also can dilate (i.e., expand) and contract in an alternating (i.e., pulsating) sequence or a peristaltic format.

A spinal CSF location of the catheter 1 can be in the lumbar spine, but can also be the cervical or thoracic spine. Alternatively, the catheter 1 can be inserted through the lumbar spine with the distal tip positioned in the thoracic or cervical spine. The catheter 1 cools the spinal cord by cooling the CSF, as well as direct spinal cord surface contact. The catheter 1 can be placed post-operatively after either a laminectomy, discectomy, or corpectomy. The catheter 1 can also be placed through a percutaneous technique similar to placement of a spinal drain or lumbar puncture. X-ray or fluoroscopy can also be used to locate the correct spinal placement of the device.

A cranial location of the catheter 1 can be the lateral ventricle of the brain. Other locations can include cerebral subdural space, cerebral subarachnoid space, spinal sabarachnoid space, cisterna magna, third ventricle, fourth ventricle, cerebral ventricles, intraventricular space, epidural space, and intracerebral space.

Figure 20:
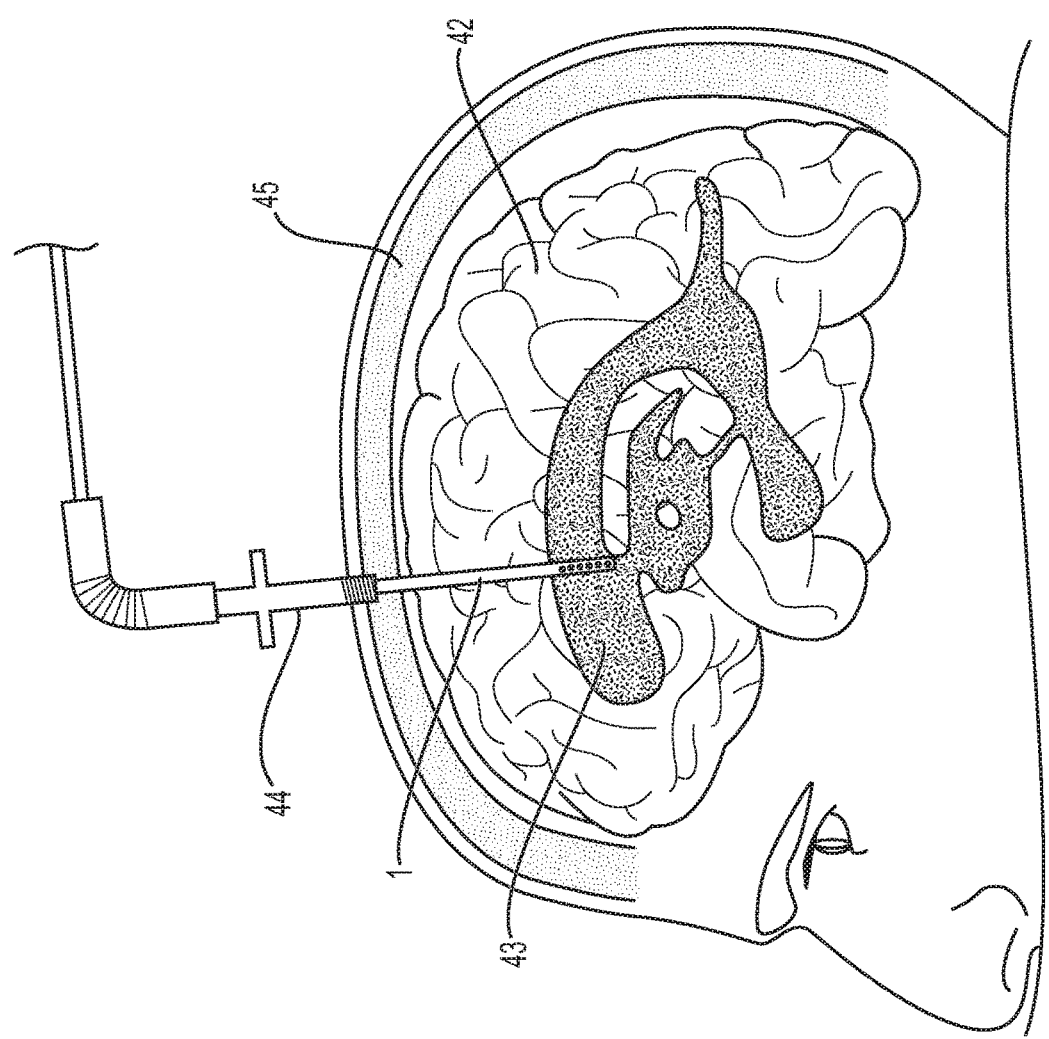
FIG. 20 is a schematic view of the flexible catheter placed in the brain lateral ventricle.

For selective brain and/or spinal cooling, the catheter 1, as shown in FIG. 20, is inserted in the ventricle 43 of the brain 42. This allows for cooling of the cerebrospinal fluid and hence the brain 42 and/or spinal cord selectively. The catheter 1 can be inserted in the lateral ventricles using the standard landmarks or can be precisely placed with stereotactic guidance or the use of an endoscope. The optional bolt 44 secures the catheter 1 to the skull 45. The catheter 1 is placed into the cerebrospinal fluid in the ventricle 43 and also allows for drainage of the cerebrospinal fluid and lowering of intracranial pressure.

Figure 21:
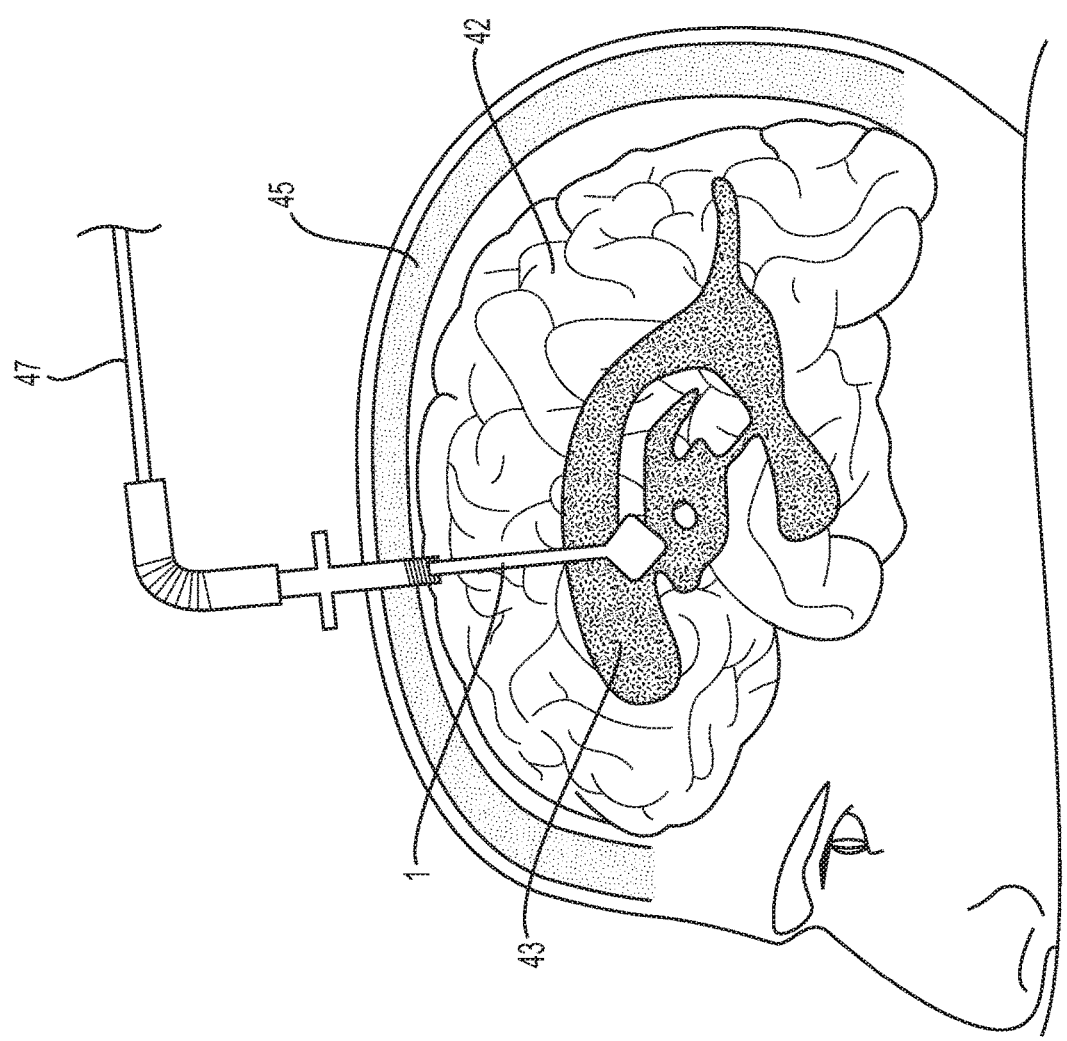
FIG. 21 is a schematic view of the flexible catheter with the distal balloon dilation capability placed in the brain lateral ventricle.

As shown in FIG. 21, the catheter 1 is placed in the ventricle 43 of the brain 42. This allows for cooling of the cerebrospinal fluid and, hence, the brain 42 and/or spinal cord selectively. The catheter 1 also comprises a balloon at the distal end to increase the surface area for accelerated heat exchange. The proximal end 47 of the catheter 1 is connected to the flow regulator and cooler 4 that circulates the coolant through the closed loop in the catheter 1. The flow regulator and cooler 4 controls the extent of coolant temperature and circulation rate. The flow regulator and cooler 4 also monitors ICP and temperature through sensors positioned near the distal portion of the catheter 1. The catheter 1 can be inserted in the lateral ventricles using the standard landmarks or can be precisely placed with stereotactic guidance or the use of an endoscope. The catheter 1 is placed into the cerebrospinal fluid in the ventricle 43 and also allows for drainage of the cerebrospinal fluid and the lowering of intracranial pressure. The distal end of the catheter 1 can also dilate (i.e., expand) and contract in an alternating (i.e., pulsating) sequence or a peristaltic format to facilitate circulation of the cooled cerebrospinal fluid.

The effects of the cooling provide for treatment of swelling, traumatic, hypoxic, and ischemic injuries. The catheter 1 is placed into the cerebrospinal fluid in the ventricle 43 of the brain 42. Typically a hole is drilled into the skull 45 to access the brain and the ventricles through a standard ventriculostomy approach.

The methodology and device described provide for treatment of any central nervous system pathology including, but not limited to, treatment of increased intracranial pressure, brain swelling or edema, spinal cord edema, trauma, brain injury, skull fracture, stroke, ischemia, hypoxia following respiratory or cardiac arrest, tumors, hemorrhage, infection, seizure, spinal cord injury, spine fractures, arteriovenous malformations, aneurysms, aortic artery surgery related spinal cord ischemia protection, thoracic and/or abdominal aortic aneurysm or dissection surgical or endovascular repair, spinal stenosis, herniated disc, and scoliosis surgery.

The catheter 1 can be inserted intracranially following the drilling of a hole in the skull via a twist drill, burr hole placement, or craniotomy/craniectomy. It can be inserted inside the spinal canal in the epidural, subdural or subarachnoid space through a percutaneous technique or following a laminotomy/laminectomy. Placement of the catheter 1 intracranially or intraspinally can be further facilitated by radiographic guidance (fluoroscopy), ventriculograms, cisternograms, myelogram with the injection of an intrathecal contrast agent through the catheter 1, ultrasound, frame based or frameless stereotactic navigation systems, or endoscopy. The catheter 1 can also comprise radio-opaque markers or be impregnated with barium to visualize correct placement in the central nervous system with x-rays.

Examples of locations for inserting the catheter 1 are in the cerebrospinal fluid space in the lateral ventricle, the subarachnoid space of the brain surface, and adjacent to the thoracic spinal cord with entry through the lumbar intrathecal space. Other locations include in the surgical resection bed following a craniotomy for the removal of a brain tumor or hemorrhage and the spinal epidural or intrathecal space following a laminectomy. The catheter 1 can also be secured to the skull by a hollow bolt. The closed loop cooling system of the catheter 1 selectively cools the central nervous system without serious side-effects of generalized body cooling and, in some embodiments, also provides for the drainage of fluid (cerebrospinal fluid or hemorrhage).

Sensors can be placed in the distal portion of the catheter 1 to be positioned inside the central nervous system. These sensors can either be in one location or in multiple locations on the catheter wall. In an embodiment, the sensors monitor pressure and temperature. In other embodiments, water sensors can also be positioned on the catheter 1 to detect cerebrospinal fluid location inside the ventricle to confirm correct catheter location, since cerebrospinal fluid predominantly comprises water. Similarly, impedance sensors on the catheter 1 can also provide confirmation of the location as the impedance changes from brain to a cerebrospinal fluid location as the catheter 1 is advanced into the lateral ventricle during placement. Other sensors on the catheter 1 can comprise cerebrospinal fluid marker sensors (i.e., cerebrospinal fluid sensors), osmolarity sensors, oxygenation sensors, carbonation sensors, metabolite sensors, and pH sensors.

The catheter 1 with the capabilities of cooling and circulating the cerebrospinal fluid provides for selective cooling of the brain and spinal cord. Since the cerebrospinal fluid is in communication from inside the brain to the outer surface of the brain and spinal cord, placement of the catheter 1 intracranially not only cools the brain but also the spinal cord. Similarly, cooling of the brain can also be achieved by placement of the catheter 1 inside the spinal canal. Alternatively, one catheter 1 can be placed intracranially and another catheter 1 in the spinal canal to increase the extent of selective central nervous system cooling.

While the embodiments and methodology described herein along with the illustrations are specific examples of the present disclosure, it is understood that the disclosure is not limited to the embodiments described herein. Numerous modifications, rearrangements, and substitutions can be made by those skilled in the art without departing from the spirit of the disclosure as set forth and defined herein.

What is claimed is:

1. A catheter for central nervous system treatment, the catheter comprising:
an outside wall;
a first inside wall; and
a second inside wall, wherein
the outside wall, the first inside wall, and the second inside wall define a first lumen,
the first inside wall and the outside wall define a second lumen,
the second inside wall and the outside wall define a third lumen,
the first lumen and the second lumen communicate at a distal portion of the catheter, the first lumen and the second lumen being adapted to have a coolant circulated therethrough, and
only a distal end portion of the outside wall defining the third lumen has one or more holes, the one or more holes allowing the third lumen to communicate with the outside environment.

2. The catheter of claim 1, wherein the outside wall is cylindrical.

3. The catheter of claim 1, wherein a distal portion of the outside wall other than the distal end portion of the outside wall defining the third lumen is expandable.

4. The catheter of claim 1, wherein a distal portion of the outside wall other than the distal end portion of the outside wall defining the third lumen comprises at least one balloon that is expandable.

5. The catheter of claim 3, wherein the distal portion of the outside wall other than the distal end portion of the outside wall defining the third lumen is capable of expanding into one or more of the following: an oval shape, a round shape, a cylindrical shape, a triangular shape, a double balloon shape, a helical shape, at an angle to the catheter, a shape of a portion of or an entire lateral ventricle, a shape of a frontal horn of a lateral ventricle, a shape of body of a lateral ventricle, a shape of an occipital horn of a lateral ventricle, a shape of a third ventricle, a shape of an operative area in a brain or spine, a shape of a cisterna magna, and a shape of a spinal canal.

6. The catheter of claim 3, wherein the distal portion of the outside wall other than the distal end portion of the outside wall defining the third lumen is expandable in a peristaltic manner.

7. The catheter of claim 3, wherein the distal portion of the outside wall other than the distal end portion of the outside wall defining the third lumen is expandable in a pulsating manner.

8. The catheter of claim 1, further comprising one or more of: a water sensor, a pressure sensor, an osmolarity sensor, a temperature sensor, an impedance sensor, an oxygenation sensor, a carbonation sensor, a metabolite sensor, a pH sensor, and a cerebrospinal fluid sensor.

9. A catheter of claim 1, wherein
the second inside wall is straight, and
the first inside wall and the second inside wall are connected.

10. The catheter of claim 9, wherein the third lumen is rectangular shaped.

11. A catheter for central nervous system treatment, the catheter comprising:
an outside wall;
a first inside wall; and
a second inside wall, wherein
the first inside wall is straight,
the second inside wall is straight,
the outside wall and the first inside wall define a first lumen,
the outside wall, the first inside wall and the second inside wall define a second lumen,
the outside wall and the second inside wall define a third lumen,
the first lumen and the second lumen communicate at a distal portion of the catheter, the first lumen and the second lumen being adapted to circulate a coolant in a closed loop through an external flow regulator connected to the catheter, and
only a distal end portion of the outside wall defining the third lumen has one or more holes, the one or more holes allowing the third lumen to communicate with the outside environment.

12. The catheter of claim 11, wherein a distal portion of the outside wall other than the distal end portion of the outside wall defining the third lumen is expandable.

13. The catheter of claim 11, wherein a distal portion of the outside wall other than the distal end portion of the outside wall defining the third lumen comprises at least one balloon that is expandable.

14. The catheter of claim 12, wherein the distal portion of the outside wall other than the distal end portion of the outside wall defining the third lumen is capable of expanding into one or more of the following: an oval shape, a round shape, a cylindrical shape, a triangular shape, a double balloon shape, a helical shape, at an angle to the catheter, a shape of a portion of or an entire lateral ventricle, a shape of a frontal horn of a lateral ventricle, a shape of body of a lateral ventricle, a shape of an occipital horn of a lateral ventricle, a shape of a third ventricle, a shape of an operative area in a brain or spine, a shape of a cisterna magna, and a shape of a spinal canal.

15. The catheter of claim 12, wherein the distal portion of the outside wall other than the distal end portion of the outside wall defining the third lumen is expandable in a peristaltic manner.

16. The catheter of claim 12, wherein the distal portion of the outside wall other than the distal end portion of the outside wall defining the third lumen is expandable in a pulsating manner.

17. The catheter of claim 11, further comprising one or more of: a water sensor, a pressure sensor, an osmolarity sensor, a temperature sensor, an impedance sensor, an oxygenation sensor, a carbonation sensor, a metabolite sensor, a pH sensor, and a cerebrospinal fluid sensor.

18. A catheter for central nervous system treatment, the catheter comprising:
an outside wall;
a first inside wall; and
a second inside wall, wherein
the outside wall, the first inside wall, and the second inside wall define a first lumen,
the outside wall and the first inside wall define a second lumen,
the second inside wall and the outside wall define a third lumen,
the first inside wall and the second inside wall are parallel to each other,
the first lumen and the second lumen communicate at a distal portion of the catheter, the first lumen and the second lumen being adapted to have a coolant circulated therethrough, and only a distal end portion of the outside wall defining the third lumen has one or more holes, the one or more holes allowing the third lumen to communicate with the outside environment.

19. The catheter of claim 18, wherein a distal portion of the outside wall other than the distal end portion of the outside wall defining the third lumen is expandable.

20. The catheter of claim 18, wherein a distal portion of the outside wall other than the distal end portion of the outside wall defining the third lumen comprises at least one balloon that is expandable.

21. The catheter of claim 19, wherein the distal portion of the outside wall other than the distal end portion of the outside wall defining the third lumen is capable of expanding into one or more of the following: an oval shape, a round shape, a cylindrical shape, a triangular shape, a double balloon shape, a helical shape, at an angle to the catheter, a shape of a portion of or an entire lateral ventricle, a shape of a frontal horn of a lateral ventricle, a shape of body of a lateral ventricle, a shape of an occipital horn of a lateral ventricle, a shape of a third ventricle, a shape of an operative area in a brain or spine, a shape of a cisterna magna, and a shape of a spinal canal.

22. The catheter of claim 19, wherein the distal portion of the outside wall other than the distal end portion of the outside wall defining the third lumen is expandable in a peristaltic manner.

23. The catheter of claim 19, wherein the distal portion of the outside wall other than the distal end portion of the outside wall defining the third lumen is expandable in a pulsating manner.

24. The catheter of claim 18, further comprising one or more of: a water sensor, a pressure sensor, an osmolarity sensor, a temperature sensor, an impedance sensor, an oxygenation sensor, a carbonation sensor, a metabolite sensor, a pH sensor, and a cerebrospinal fluid sensor.

25. A method for treatment of a central nervous system, the method comprising:
    inserting a catheter into the central nervous system, the catheter including:
        an outside wall;
        a first inside wall; and
        a second inside wall, wherein
        the outside wall, the first inside wall, and the second inside wall define a first lumen,
        the first inside wall and the outside wall define a second lumen,
        the second inside wall and the outside wall define a third lumen,
        the first lumen and the second lumen communicate at a distal portion of the catheter, and
        only a distal end portion of the outside wall defining the third lumen has one or more holes, the one or more holes allowing the third lumen to communicate with the outside environment; and
    circulating a coolant through the first lumen and the second lumen.

26. The method of claim 25, wherein the treatment of the central nervous system addresses one or more of: traumatic brain injury, spine trauma, ischemia, hypoxia, seizure, hemorrhage, tumor, infection, cranial surgery, increased intracranial pressure, cerebral swelling, spinal cord injury, ischemia, hypoxia, swelling, aortic aneurysm surgery or endovascular treatment, aortic dissection surgery or endovascular treatment, cross clamping of aorta, tumor, infection, scoliosis surgery, and spine surgery.

27. The method of claim 25, wherein the inserting of the catheter is accomplished by one or more of: craniotomy, burr hole, twist-drill hole, laminectomy, laminotomy, percutaneously, endoscope assisted, stereotactic guidance, x-ray guided, fluoroscopy, intrathecal contrast agent, ultrasound guidance, and radio-opaque markers.

28. The method of claim 25, wherein the inserting of the catheter comprises inserting the catheter into one or more of: cerebrospinal fluid, intraventricular, lateral ventricle, cerebral subarachnoid, spinal subarachnoid, cerebral subdural, intrathecal, epidural, intracerebral, cisterna magna, third ventricle, and fourth ventricle.

29. The method of claim 25, further comprising at least one of draining cerebrospinal fluid via the third lumen or performing pressure monitoring of the central nervous system via the third lumen.

30. The method of claim 25, further comprising:
    draining cerebrospinal fluid via the third lumen; and
    regulating the draining of the cerebrospinal fluid by one or more of: a valve that opens at a set pressure, an anti-reflux valve, an automated collection chamber that allows fluid drainage at a set pressure, a drainage bag that allows fluid drainage at a set pressure based on location of a bag relative to anatomical landmarks.

31. The method of claim 25, further comprising performing selective hypothermia of the central nervous system with the circulating of the coolant.

32. The method of claim 31, wherein the performing of the selective hypothermia comprises adjusting a temperature of the coolant during the circulating of the coolant.

33. The method of claim 31, wherein the performing of the selective hypothermia comprises adjusting a flow rate of the coolant during the circulating of the coolant.

34. The catheter of claim 1, wherein one of the first inside wall and the second inside wall contacts the distal portion of the catheter, and the distal portion of the catheter and a terminal end of another of the first inside wall and the second inside wall have a gap formed therebetween.

* * * * *